United States Patent [19]

Makin et al.

[11] 4,181,675
[45] Jan. 1, 1980

[54] PROCESS FOR METHANOL PRODUCTION

[75] Inventors: Earle C. Makin; K. Keith Okamoto, both of Dickinson, Tex.

[73] Assignee: Monsanto Company, St. Louis, Mo.

[21] Appl. No.: 943,841

[22] Filed: Sep. 19, 1978

[51] Int. Cl.$^2$ .............................................. C07C 29/16
[52] U.S. Cl. ................................... 260/449.5; 55/16; 55/158; 48/DIG. 5
[58] Field of Search ................. 260/449.5; 55/16, 158; 48/DIG. 5

[56] References Cited

U.S. PATENT DOCUMENTS

| | | | |
|---|---|---|---|
| 3,186,145 | 6/1965 | Pelton et al. | 260/449.5 |
| 3,442,002 | 5/1969 | Geary et al. | 55/158 |
| 3,598,527 | 8/1971 | Quartulli et al. | 260/449.5 |
| 3,940,428 | 2/1976 | Connell et al. | 260/449.5 |
| 3,950,369 | 4/1976 | Gent | 260/449.5 |
| 4,051,300 | 9/1977 | Klein et al. | 428/398 |

OTHER PUBLICATIONS

Gardiner et al., Chem. Eng. Prog. Oct. 1977, pp. 76–78.

*Primary Examiner*—Howard T. Mars
*Attorney, Agent, or Firm*—Thomas B. Leslie

[57] ABSTRACT

An improved methanol synthesis process is provided wherein synthesis gas containing hydrogen and carbon dioxide is passed over a methanol synthesis catalyst, cooled to condense methanol and water in the reacted gas, the liquids separated, a purge gas stream removed while the remaining reacted gas is recycled to the synthesis catalyst, the purge gas separated by contacting the outer surfaces of a plurality of hollow fiber membranes selectively permeable to hydrogen and carbon dioxide to form a permeant gas depleted in hydrogen and carbon dioxide and a permeate gas enriched in said gases and the enriched permeate gas is combined with the synthesis gas. In an optional embodiment, methanol vapor is first recovered from the purge gas prior to contacting the selectively permeable membranes, preferably by a water scrub.

30 Claims, No Drawings

PROCESS FOR METHANOL PRODUCTION

This invention relates to a process for producing methanol and in particular such process wherein the yield of methanol is improved by the employment of semi-permeable hollow fiber membranes.

In the past many processes have been suggested for the synthesis of methanol from gaseous mixtures of carbon oxides and hydrogen. Most of such suggested processes have involved a catalytic reaction conducted at relatively high pressures and temperatures over a large number of different metallic and metallic oxice catalysts and mixtures of such catalysts. In recent years processes have been developed for the catalytic synthesis of methanol in the lower range of such elevated pressures and temperatures, such as those processes operating at pressures of below 150 atmospheres and at temperatures up to about 300° C.

In general, all such processes produce relatively low yields of the desired methanol in each single passage over a catalyst bed. Consequently they all involve the separation of the product methanol by liquifaction thereof and the recycle of the uncondensed gaseous reaction mixture, usually with additional fresh synthesis gas mixtures, for repeated contact with the methanol synthesis catalyst. The synthesis gas mixtures for all such methanol synthesis processes are composed of hydrogen and carbon monoxide or carbon dioxide or both. In practice all such synthesis gas mixtures also usually contain relatively small amounts of various inert gases such as methane and possibly nitrogen or argon. Consequently, all such methanol synthesis processes have provisions for purging in order to remove the inert gases and prevent buildup thereof through repeated recirculation of recovered reaction gas mixtures and added fresh synthesis gas mixtures. Recovered reaction gas mixtures will also contain small amounts of methanol vapor uncondensed and not removed as liquid therefrom. The purge gas removed from the process necessarily contains a much higher percentage of reactive synthesis gases such as hydrogen, carbon monoxide and carbon dioxide than of inert gases. It will also contain a small percentage of uncondensed methanol vapor which is not removed by the liquifaction step. All these reactive synthesis gases and unrecovered methanol vapor represent losses in yield of the desired methanol product.

Various uses for the purged gases have been suggested in the past. These have included use of the purged gases as fuel, especially for supplying heat for a reformer utilized as a source of a synthesis gas mixture, by addition to a hydrocarbon feedstream to a reformer and as a source of hydrogen for the hydrodesulfurization of reformer feed. None of these suggested uses, however, makes use of the purged synthesis gases for the direct synthesis of additional methanol product, and none recovers that portion of methanol vapor removed with the purged gas stream.

One method for recovering a part of the carbon oxide values present in a methanol process purge gas stream is suggested by Connell and Pinto in U.S. Pat. No. 3,940,428. In this process the inventors suggest the absorption of the carbon oxides into a scrubbing liquid from which the carbon oxides can be regenerated by heating and subsequently blended with or added to the synthesis gas feed stream. The hydrogen, methane and any other constituent gases in the purge gas stream are then directed to fuel use or made available for other uses. Even in this process losses in values of methanol synthesis gas are still considerable and improved processes for recovery of these values are highly desirable.

We have now found that a methanol synthesis process utilizing semi-permeable hollow fiber membranes for the recovery of significant amounts of the synthesis gas values present in a purge gas stream provides an improved synthesis process with significantly increased yield of methanol product.

According to the invention there is provided a methanol production process in which synthesis gas comprising hydrogen and carbon dioxide is passed over a methanol synthesis catalyst, cooled to condense and remove methanol and water contained in a gas mixture, a portion of uncondensed gases are removed as purge and passed into contact with the outer surfaces of a plurality of semi-permeable hollow fiber membranes selectively permeable to hydrogen and carbon dioxide and the permeated gas concentrated in hydrogen and carbon dioxide is combined with a synthesis gas mixture for contact with the methanol synthesis catalyst. Alternatively, prior to contacting the purge gas stream with the semipermeable hollow fiber membranes such stream is treated to recover any methanol present as vapor. This treatment may take the form of cooling by chilled liquid in heat exchange, refrigeration or the like to condense substantially all of the remaining vaporous methanol. It may also comprise adsorption on a solid adsorbent such as activated carbon or silica, or absorption by an absorbing liquid. Most preferably, such alternative treatment will comprise scrubbing with water as absorbent since the recovery of methanol vapor is essentially complete with a water scrub.

It has been found that substantial advantages are inherent in the process for methanol synthesis wherein the purge gas stream is subjected to permeation through semipermeable hollow fiber membranes selectively permeable to hydrogen and carbon dioxide. The predominant portion of the hydrogen and of the carbon dioxide present in the purge gas stream are recovered in the form of a permeated gas stream which is suitable for reintroduction to the process thereby increasing the yield of methanol product. Because such permeation provides for recovery of predominant portions of these gases an increased rate of purge is desirable, which assures the removal of sufficient amounts of the inert gases such as methane and nitrogen to balance such withdrawal with new portions charged with the synthesis gas feed and prevents the buildup of such inert gases in the system. Contact of the purge gas stream with the outer surfaces of the preferred large internal diameter hollow fiber membranes discussed below also provides that the permeated gas stream of recovered hydrogen and carbon dioxide gases be at a sufficient pressure relative to the pressure of the purge gas stream that it can be reintroduced into the synthesis process with a minimum amount of additional compression required. The increased purge rates desired for balance of inert gases within the system do not exact any penalty in the form of lost methanol product values if the optimal alternative of scrubbing the purge gas stream with water absorbent prior to its separation over the hollow fiber membranes is employed since the water scrubbing will recover essentially all of the methanol vapor present in the purge stream.

In accordance with the present invention it is preferred that the purge gas stream to be permeated contact the outer surface of hollow fiber membranes having somewhat larger internal and external diameters than those previously preferred by the prior art. In most previous hollow fiber membrane separation devices designed for contacting gas streams the desire for very large membrane active surface areas for contact with such gas streams have led the developers to prescribe very small hollow fibers as membranes with small outside and inside diameters. For example, in U.S.P. 3,339,341, Maxwell et al teach that hollow fibers having outside diameters of between 20 and 250 microns are especially preferred, see Col. 4, lines 65–70 and at Col. 14, line 63 where they record that a semi-commercial installation utilized hollow fibers of 29.2 microns inside diameter. Others have similarly found that hollow fibers having relatively small outside diameters are advantageous for utilization in separation apparatus in order to provide sufficiently large membrane surface areas and other advantages such as capacity to withstand relatively large pressure differentials. For example, Mahon in U.S. Pat. No. 3,228,877 teaches that hollow fibers should have relatively small outside diameters and that the more advantageous range of such outside diameters is between 10 and 50 microns see Col. 11, lines 4–20.

When applied to the separation of gaseous mixtures in practice, though, it has been found that the small inside and outside diameter hollow fiber membranes frequently suffer a severe disadvantage in the extent of pressure drop experienced both along and through such hollow fiber membranes, whereas it is generally desirable that the streams of separated gases be maintained as pressures which are substantial percentages of initial pressure of the gas stream to be separated. Thus, it is generally desired to minimize pressure drop across the membrane separation apparatus, so long as this is consistent with sufficient pressure drop across the semi-permeable membrane itself as to maintain good rates of permeation for permeating gases. For example, in the prior art it has been shown by Gardner et al in *Chemical Engineering Progress* October 1977, pages 76–78 that large pressure drops are commonly encountered. Thus, in FIG. 4, page 77 in relation to a process using hollow fiber membranes for separating hydrogen and carbon monoxide feed stream that the pressure drop along the length of the very small diameter fiber bores is some 45 percent of the initial 422 kg/cm$^2$ (600 psig) pressure and the pressure drop in the permeated gas stream passing through such membranes amounts to 83.5 percent of the original pressure.

Such extensive pressure drops are often undesirable because of the substantial cost involved in recompressing such gas streams to pressures required for subsequent processing or other use.

In contrast, it has now been found that for purposes of improved axial or radial flow through a bundle of hollow fibers those of somewhat larger outside and inside diameters are desired. For example, it has been taught by Leonard in U.S. Pat. No. 855,850 filed Nov. 30, 1977, which co-pending application is incorporated herein by reference, at page 10, line 29 to page 11, line 11 that hollow fibers having outside diameters of from about 150 to 800 microns are preferred for most fluid separations, particularly gas separations. It is also taught by Leonard in the above application that the preferred wall thickness of hollow fibers falls within the range of about 50 to 300 microns, and that such hollow fibers are preferably fabricated from a material having a tensile modulus of at least about 15 kg/cm$^2$, see page 15, lines 4–17. Also taught by Leonard is the fact that hollow fibers having low amplitude crimps result in fibers which exhibit relatively high packing factors, e.g. at least 40 percent, while maintaining acceptable flow axially and radially of a bundle of such fibers, see page 9, line 8 to page 10, line 28, and page 12, line 30 to page 14, line 26.

Advantages have been found in the use of hollow fiber membranes when such membranes have relatively large outside diameters and wall thicknesses as described above. These advantages are best observed when the feed gas mixture is fed radially or axially. By radial feed is meant that the gas mixture is introduced in the mid portion of a bundle of hollow fibers and flows substantially perpendicularly to the orientation of the hollow fibers. By axial feed is meant that the gas mixture is introduced at an outside portion of the fiber bundle, flows generally in the same direction as the orientation of the fibers, and exits at another portion of the fiber bundle. Though often radial feed is considered to provide better gas separation efficiencies, axial feed is frequently more desirable since the separation apparatus may be less complex in design than radially fed separation apparatus. Since no radial feed conduit need be positioned within the bundle, the bundles employed for axial flow may comprise a greater ratio of available membrane surface area for a given volume of separation apparatus than that of a radially fed apparatus. Shell side feed to hollow fiber separation apparatus can provide certain advantages. For instance, a greater surface area for effecting the separation is provided at the exterior surfaces of hollow fibers than at the interior surface of those fibers. Moreover, hollow fibers are generally able to withstand higher pressure differentials when the higher pressures are on the exterior as opposed to the interior of the fibers since generally most materials exhibit greater compressive than tensile strength. In accordance with the present invention it has been found that the improved methanol synthesis process is most advantageously carried out when the separated portion of the uncondensed reaction gases, i.e. the purge gas stream, is contacted with the outside or shell side of the hollow fiber membranes positioned in bundles within separation apparatus vessels arranged for radial or more preferably axial flow, and in which the desired permeate gas stream of concentrated hydrogen and carbon dioxide is withdrawn from the bores of said hollow fiber membranes.

For convenience the present invention will be described in detail in relation to a so-called low pressure methanol process in which the methanol synthesis is carried out at a pressure below 150 atmospheres and at a temperature of up to 300° C. It is to be understood, however, that the same procedures for the recovery of synthesis gas values and optionally of methanol vapor can be applied to a purge gas stream from any other methanol synthesis processes which require or are susceptible to the removal of a purge of a portion of the gaseous reaction mixture, including those processes operating at higher pressures and temperatures. Thus the present invention is not limited to the specifically described methanol synthesis process detailed hereinafter.

Methanol synthesis processes normally will include a synthesis gas generation stage which comprises a primary reforming reaction of gaseous or liquid hydrocarbons such as natural gas, naphtha, gas oil or the like. The primary reforming reaction is usually a catalytic steam reforming which is employed to produce the desired mixture of hydrogen and carbon oxides for the synthesis of methanol. The content of various product gases will vary with the nature of the reacting hydrocarbon and the type of reforming reaction and the nature of the catalyst employed. For example, when natural gas is employed and reformed over the usual catalysts, various other gases than hydrogen, carbon monoxide and carbon dioxide are present, such as methane, nitrogen and water. Other sources of the necessary constituent synthesis gases under pressure can, of course be employed if available as by-products of refining and/or petrochemical operations. In general, by-product sources of hydrogen and carbon oxides are not available in sufficient relative quantities or are grossly contaminated with other gases which render them unsuitable for the synthesis of methanol.

In order not to poison the methanol synthesis catalyst or reduce the effectiveness of that reaction the compounds of sulfur present in the hydrocarbons being subjected to reforming must first be removed and this is particularly necessary when natural gas from the usual pipeline sources is employed as a reformer feed. Depending upon the presence of sulfur therein the liquified alkanes and normally liquid hydrocarbons also suitable as reformer feeds may also require removal of such sulfur content. This is normally accomplished by subjecting such hydrocarbon feed to a hydrosulfurization reaction using any convenient source of hydrogen. The reformer feeds may also be freed of their sulfur content by other sulfur removal processes as well.

The synthesis gas produced by the usual steam reforming reaction is first freed of its large water vapor content by cooling, condensing and separating the liquified water therefrom. Thereafter this synthesis gas is compressed to the desired pressure for the methanol synthesis process. It is also generally heated by heat exchange with hot reaction gases from the catalytic methanol synthesis. Synthesis gas is then passed into the methanol synthesis reactor to contact the methanol synthesis catalyst. The catalysts generally employed for synthesis of methanol are copper based catalysts, especially those containing copper, zinc and a third component which is chromium or the oxide of at least one metal from Groups II to IV of the periodic table, especially aluminum or magnesium.

After passage through the catalyst bed the reaction gases are cooled by passage through a heat exchanger in which the synthesis gas is heated and further cooled to condense the methanol content. Thereafter the mixture of liquid and gases are passed to a separator vessel to separate and recover the liquid methanol produced.

In all processes for methanol synthesis a purge of inert gases such as methane, nitrogen and argon is required. A large part of the purged gases is generally hydrogen, particularly when the synthesis gas is prepared by reforming natural gas or one of the lighter alkanes. In addition to hydrogen the purged gases also consist of uncondensed methanol, carbon dioxide, carbon monoxide as well as unreacted methane and other inert gases. In most processes the purge of the synthesis reaction gases prior to recycle is made after the separation of all liquid methanol condensed from the reaction gases. In the present process the purge stream is removed after the uncondensed reaction gases have been separated from the liquified methanol.

In one alternative aspect of the present invention this purge stream is treated to recover the methanol vapor present in saturation or near saturation amounts in the reaction gases. As indicated above, such treatment may comprise additional cooling and separation of condensed methanol, adsorption onto solid adsorbents such as activated carbon or silica or absorption by liquid absorbents. In an optimized process the uncondensed methanol vapor present is recovered by means of a water scrub. Because only the purge gas stream is scrubbed the scrubber can be of economical size. The methanol-water stream from such scrubber is sent to a methanol distillation column associated with the methanol synthesis process. Because of the small volume of this methanol-water stream it will add very little to the load of the distillation column to which it is fed.

Recovery of the methanol vapor present in the purge gas stream reduces the volume of methanol vapor in the purge gas to very low levels. It thus contributes to the extended life of the hollow fiber membranes subsequently contacted by the purge gas. Some polymer membranes have been found to be sensitive to concentrations of methanol vapor at or near saturation. Desirably, such treatments as a water scrub will reduce the concentration of methanol vapor to less than 20 percent of saturation and preferably to less than 10 percent of saturation in the purge gas stream prior to contact thereof with the fiber membranes.

It has also been found desirable to remove from the purge gas stream any liquid droplets which may have been entrained in the gases from the methanol separator or the optional water scrubber or condensed by cooling of the purge gas line. This may be conveniently accomplished by passage of the purge gas through a demister or similar packed vessel for removal of such entrained liquids.

The purge gas stream, preferably after substantial removal of methanol vapor therefrom is contacted with the semi-permeable hollow fiber membranes for separation into an inert gas and hydrogen stream for a fuel use and a hydrogen and carbon dioxide concentrate for recycle to the methanol synthesis. For contact with the semi-permeable membranes the purge gas stream will be at essentially the pressure of the gas/liquid separator, and in a typical low pressure methanol synthesis process from about 30 to about 100 atmospheres. Preferably the purge gas will be at a pressure of from about 40 to 55 atmospheres and typically at about 44 to 47 atmospheres. The purge gas stream will generally be at a temperature of from about 10° to about 50° C., preferably at from 20° to 45° C. and typically at about 40° C.

The purge gas stream is contacted with a hollow fiber separation membrane which exhibits selectivity to the permeation of hydrogen and carbon dioxide as compared to the permeation of methane and the other inert gases present, if any, such as nitrogen and possibly argon. In view of the generally substantially higher volume concentration of hydrogen in the purge gas stream as compared to that of methane, the separation methane need not exhibit high selectivity for separation of hydrogen from methane in order to provide for an effective purging of the methane and recovery of the hydrogen and carbon dioxide values in such purge stream. Generally, the selectivity for separation of a membrane is described in terms of the ratio of the permeability of the fast permeating gas, i.e. hydrogen, to the permeability of the slow permeating gas, i.e. methane, wherein the permeability of the gas through the membrane can be defined as a volume of gas, at standard temperature and pressure which passes through the membrane per square centimeter of surface area per second for a partial pressure drop of 1 centimeter of mercury across the membrane per unit thickness. This ratio is referred to as the separation factor of a membrane for the specific gases the permeability of which are used. Desirably, the separation factor of the selected membranes for hydrogen over methane is at least about 10. Separation factors for hydrogen over methane of 80 or 100 or greater may be provided by certain membranes. For the concentration of carbon dioxide in the permeated gas stream the selected membranes should also possess a separation factor for carbon dioxide over methane of from 2 to about 50 and preferably from about 5 to 25. The higher the permeability of hydrogen and carbon dioxide through the selected membrane, the less effective membrane surface area is required to pass the desired amounts of hydrogen and carbon dioxide and substantially reject the methane present in the purge gas stream. Particularly desirable membranes exhibit hydrogen permeabilities of at least $1 \times 10^{-6}$, preferably at least $1 \times 10^{-5}$ to $1 \times 10^{-4}$ cubic centimeters of hydrogen per square centimeter of membrane surface area per second at a partial pressure drop of 1 centimeter of mercury across the membrane. Likewise, particularly desirable membranes for use in this process also exhibit carbon dioxide permeabilities of at least about $1 \times 10^{-6}$ and preferably $5 \times 10^{-6}$ to $5 \times 10^{-5}$ cu. centimeters of carbon dioxide per square centimeter of membrane surface area per second at a partial pressure drop of 1 centimeter of mercury across the membrane.

The most effective membrane surface area is an area sufficient to permeate as much as possible of the desired hydrogen and carbon dioxide gases present while rejecting to the shell or permeant gas stream desired amounts of the inert gases present in the purge gas stream. Generally this will be an amount of methane sufficient to balance the methane coming into the methanol synthesis process from the stream reforming operation. Factors influencing the determination of the amount of effective membrane surface area include the relative permeation rate of hydrogen and carbon dioxide as well as that of methane through the membrane under the separation conditions including temperature, absolute pressure, and partial pressure differentials of the hydrogen, carbon dioxide and methane gases across the membrane.

Partial pressure differentials of hydrogen and carbon dioxide across the membrane provide the driving force for the permeation of hydrogen and carbon dioxide and depend not only on the total pressure but on the concentration of hydrogen and carbon dioxide on each side of the membrane. Advantageous pressure differentials across the membrane are at least about 3 atmospheres of hydrogen. In many instances hydrogen pressure differentials across the membrane can be considerably greater, from about 5 to about 50 atmospheres and preferably from about 6 to about 30 atmospheres. Sufficient effective membrane surface area and pressure differential is provided that at least about 25 percent and preferably from about 30 to about 80 percent of the hydrogen in the purge gas stream permeates the separation membrane.

In the present invention the separator vessel contains membranes in hollow fiber membrane form with a plurality of the hollow fiber membranes arranged substantially parallel in bundle form. The purge gas stream is contacted on the outside surfaces (shell side) of the hollow fiber membranes and either radial or preferably axial flow along and about the hollow fiber membranes is established. Shell side effluent or permeant gas mixture from the separator can be within 1 to 3 atmospheres of the pressure of the purge gas stream fed to the separator. Hence very little pressure drop is experienced on the shell side of the hollow fiber membranes in either radial or axial flow. If preferred axial flow is employed the present process is found to be advantageous either in concurrent or countercurrent mode, although it is most preferred to operate in a countercurrent manner. Thus, by establishing countercurrent flow by admitting the purge gas stream at the end of a hollow fiber membrane separator from which the bore effluent product is removed an increased hydrogen partial pressure differential across the hollow fiber membranes is maintained since the concentration of hydrogen increases in the bore as it flows in the direction in which the higher concentration of hydrogen is present in the purge gas stream.

The separator containing the hollow fiber separation membranes may be of any suitable design for gas separations, providing for shell side radial or more preferably axial flow about the hollow fiber membranes. Thus the separator vessel may be either single or double-ended radial flow design wherein the purge gas stream is admitted to a gas feed conduit positioned at the center of the fiber membrane bundle, the permeate gas product is withdrawn from the bores of the hollow fibers at either one or both ends of the vessel, and the permeant gas is removed from either one or both ends of the shell of the separator vessel.

For use in shell side axial flow the separator vessel may be of double ended design wherein the purge gas stream is admitted in the mid portion of the shell of the separator vessel and the permeant gas removed from both ends of the shell while the permeate gas stream may be removed from the bores of the hollow fibers at either one or both ends of the separator vessel. More preferably the separator vessel is of single-ended design in which the permeate gas from the bores is removed from one end only and the permeant gas can be removed from either end of the separator vessel while the purge gas can be admitted to the separator vessel at any point from one end to the opposite end of the shell. In order to establish the most desirable countercurrent flow it is preferable to admit purge gas at the same end of the separation vessel at which the permeate gas from the bores is removed and to remove the permeant gas mixture from the opposite end of the separator vessel.

Any suitable material selectively permeable to hydrogen and carbon dioxide in favor of methane and other inert gases may be employed for the hollow fiber separation membrane. Typical membrane materials include organic polymers or organic polymers mixed with inorganics such as fillers, reinforcements, and the like. Metallic and metal-containing membranes may also be employed. Polymers which may be suitable for the separation membranes can be substituted or unsubstituted polymers and may be selected from polysulfones; polystyrenes, including styrene-containing polymers such as acrylonitrile-styrene copolymers, styrene-butadiene copolymers and styrene-vinylbenzylhalide copolymers; polycarbonates; cellulosic polymers, such as cellulose acetate, cellulose acetate-butyrate, cellulose propionate, ethyl cellulose, methyl cellulose, nitrocellulose, etc.; polyamides and polyimides, including aryl polyamides and aryl polyimides; polyethers; polyarylene oxides, such as polyphenylene oxide and polyxylylene oxide; polyesteramide-diisocyanates; polyurethanes; polyesters, including polyacrylates, such as polyethylene terephthalate, polyalkyl methacrylates, polyalkyl acrylates, polyphenylene terephthalate, etc.; polysulfides; polymers from monomers having alpha-olefinic unsaturation other than mentioned above such polyethylene, polypropylene, polybutene-1, poly-4-methylpentene-1, polyvinyls, e.g. polyvinylchloride, polyvinylfluoride, polyvinylidene chloride, polyvinylidene fluoride, polyvinyl alcohol, polyvinyl esters such as polyvinyl acetate and polyvinyl propionate, polyvinyl pyridines, polyvinyl pyrrolidones, polyvinyl ethers, polyvinyl ketones, polyvinyl aldehydes such as polyvinyl formal and polyvinyl butyral, polyvinyl amides, polyvinyl amines, polyvinyl urethanes, polyvinyl ureas, polyvinyl phosphates and polyvinyl sulfates; polyallyls; polytriazoles; polybenzobenzimidazoles; polycarbodiimides; polyphosphazines; etc., and interpolymers including block interpolymers containing repeating units from the above such as terpolymers of acrylonitrile-vinyl bromide-sodium salt of para-sulfophenylmethallyl ether; and grafts and blends containing any of the foregoing. Typical substituents providing substituted polymers include halogens such as fluorine, chlorine and bromine; hydroxyl groups; lower alkyl groups; lower alkoxy groups; monocyclic aryl; lower acyl groups and the like.

The hollow fiber membrane material is preferably as thin as possible in order to improve the rate of permeation through the membrane, yet of sufficient thickness to insure adequate strength to the hollow fiber membrane to withstand the separation conditions, including the differential pressures and differential partial pressures employed. Hollow fibers membranes may be isotropic, i.e. have substantially the same density throughout, or they may be anisotropic, i.e. having at least one zone of greater density than at least one other zone of the fiber membrane. The hollow fiber membrane may be chemically homogenous, i.e. constructed of the same material, or it may be a composite membrane. Suitable composite membranes may comprise a thin layer which effects the separation on a porous physical support which provides the necessary strength to the hollow fiber membrane to withstand the separation conditions. Other suitable composite hollow fiber membranes are the multicomponent hollow fiber membranes disclosed by Henis et al in Belgian Pat. No. 860,811, published May 16, 1978 and herein incorporated by reference. These membranes comprise a porous separation membrane which substantially effects the separation and a coating material in occluding contact with the porous separation membrane. These multicomponent membranes are particularly attractive for gas separations including those for separating hydrogen and carbon dioxide from methane, carbon monoxide, nitrogen and other inert gases, in that good selectivity of separation and high flux through the membrane can be obtained.

The materials for the coating of these multicomponent membranes may be natural or synthetic substances, and are often polymers, which advantageously exhibit the appropriate properties to provide occluding contact with the porous separation membrane. Synthetic substances include both addition and condensation polymers. Typical of the useful materials which can comprise the coating are polymers which can be substituted or unsubstituted, and which are solid or liquid under gas separation conditions, and include synthetic rubbers; natural rubbers; relatively high molecular weight and-/or high boiling liquids; organic prepolymers; polysiloxanes, silicone polymers; polysilazanes; polyurethanes; polyepichlorhydrins; polyamines; polyimines; polyamides including polylactams; acrylonitrile-containing copolymers such as poly ($\alpha$-chloroacrylonitrile) copolymers; polyesters including polyacrylates, e.g. polyalkylacrylates and polyalkyl methacrylates wherein the alkyl groups have from 1 to about 8 carbon atoms, polysebacates, polysuccinates, and alkyd resins; terpinoid resins; linseel oil; cellulosic polymers; polysulfones, especially aliphatic-containing polysulfones; polyalkylene glycols such as polyethylene glycol, polypropylene glycol, etc.; polyalkylene polysulfates; polypyrrolidones; polymers from monomers having $\alpha$-olefinic unsaturation such as polyolefins, e.g. polyethylene, polypropylene, polybutadiene, poly(2,3-dichlorobutadiene), polyisoprene, polychloroprene, polystyrene including polystyrene copolymers, e.g., styrene-butadiene copolymers, polyvinyls such as polyvinyl-alcohols, polyvinyl aldehydes, e.g. polyvinyl formal and polyvinyl butyral, polyvinyl ketones, e.g. polymethylvinylketone, polyvinyl esters, e.g. polyvinyl benzoate, polyvinyl halides, e.g. polyvinyl bromide, polyvinylidene halides, polyvinylidene carbonate, poly(N-vinylmaleamide), etc., poly(1,5-cyclooctadiene), poly(methylisopropenylketone), fluorinated ethylene copolymers, polyarylene oxides, e.g. polyxylylene oxide; polycarbonates; polyphosphates, e.g. polyethylenemethyl phosphate; and the like, and any interpolymers including block interpolymers containing repeating units from the above and grafts and blends containing any of the foregoing. The polymers may or may not be polymerized after application to the porous separation membrane.

In the present process the desired recovered methanol synthesis gas mixture comprising those gases permeated through the hollow fiber membranes is withdrawn from the bore of such membranes. The gas mixture has a much enhanced proportion of hydrogen and a substantial proportion of the carbon dioxide present in the purge gas stream removed from the recycled uncondensed reaction gas stream with substantially all of the methane and inert gases excluded therefrom. The permeated recovered gas mixture has been found to possess a relatively consistent composition of more than 85 mole percent hydrogen despite relatively wide variations in the mole percentages of the specific gases comprising the purge gas streams. It has also been found that despite a wide variation in the mole percentages of methane contained in such purge gas streams approximately 90 and often 95% of the methane and inert gases are rejected by the membranes and excluded from permeated recovered synthesis gas mixtures.

Any purge gas composition in which substantial amounts of the hydrogen and carbon dioxide content are to be enhanced in respect to the other gaseous components therein can be treated by the present process. Generally such purge gases range in hydrogen to methane ratios of from about 2:1 up to 20:1. Likewise they will range in hydrogen to carbon dioxide ratios of from about 5:1 to 20:1. Any desired flow rate can be maintained in the separator vessels employed in the present process by varying the size and number of such vessels employed.

The differential in pressure maintained between the purge gas stream contacting the outside of the hollow fiber membranes and the permeate stream within the bores of such membranes is a major variable involved in the present process, since it has been found to normally effect the volume percent of hydrogen and carbon dioxide present in the purge gas stream which can be recovered in the permeated gas product. Thus it has been found that the pressure differential may range from as low as about 3 to as high as about 100 atmospheres, depending upon the inherent strength and resistance to rupture of the hollow fiber membranes employed. Preferably such differential will range from about 5 to about 50 atmospheres, and most typically from about 6 to about 40 atmospheres. The pressure of the purge gas stream contacting the shell side of the hollow fiber membranes can range from as low as 5 to about 100 atmospheres, and preferably ranges from about 5 to about 60 atmospheres and more preferably from about 7 to about 50 atmospheres. In contrast the pressure on the permeate gas stream in the bores of the hollow fiber membranes can range from as low as 1 to 95 atmospheres, preferably from about 5 to 55 atmospheres and typically from about 10 to about 30 atmospheres.

The permeated recovered methanol synthesis gas stream produced by the membrane separator treatment of the purge gas stream has been found to be suitable and advantageous for recycle to the methanol synthesis gas stream contacting the synthesis catalyst. Since the treatment of the purge gas stream by permeation of a portion thereof through the hollow fiber membranes has induced a pressure drop such permeated gas stream would require recompression before it could be combined with the recycle of the remaining uncondensed reaction gases for makeup with fresh synthesis gas and recontact with the methanol synthesis catalyst. In order to minimize the cost of compression it has been found advantageous to maintain a sufficient pressure upon the gas stream in the bores of membrane such that the permeated recovered gas stream can be combined with a stream of fresh synthesis gas mixture during its compression cycle. Thus, it has been found advantageous to maintain the pressure on the permeated recovered synthesis gas stream at approximately the pressure existing in the fresh synthesis gas stream between two stages of compression thereof. For example, if the fresh methanol synthesis gas is compressed in a first stage to about 25 atmospheres and in a second stage to about 45 atmospheres the permeated recovered gas stream can be conveniently combined with the fresh synthesis gas stream between the two stages of compression if the permeated gas stream is maintained at a pressure of about 25 atmospheres. The maintenance of such a pressure which still provides for a sufficiently large pressure drop for the recovery of the desired amounts of hydrogen and carbon dioxide has been found to be practical and desirable.

Although the permeated recovered methanol synthesis gas stream is entirely suitable for combining with the overall methanol synthesis gas mixture, such recovered permeated gas stream normally demonstrates an excess of hydrogen over that needed to react stoichiometrically with the carbon dioxide and carbon monoxide present in the recovered gas stream. In order that such recovered synthesis gas values will produce the optimum amount of desired methanol product it has been found desirable to supplement the permeated recovered gas stream with sufficient carbon dioxide to stoichiometrically balance the hydrogen present. This can be accomplished by adding sufficient carbon dioxide from any convenient source outside the present process. That source can typically comprise a gas stream of high carbon dioxide content which may be available as by-product from some other industrial process. Such gas stream should contain little or none of the undesired methane or inert gases. For optimum results the added carbon dioxide rich stream should be brought to the same approximate pressure as the permeated recovered gas stream prior to combining therewith.

There is simultaneously produced a permeant or shell effluent gas stream from the outside of the hollow fiber membranes comprising the remainder of the gases present in the purge gas stream and of a relatively higher methane and inert gas content. Generally this methane rich permeant stream will comprise at least 50% hydrogen and contain approximately 90 or more percent of the methane and inert gases present in the initial purge gas stream. This methane rich permeant gas stream is suitable for any desired use in a particular installation. In many instances its optimum use may be as supplemental fuel gas to the furnace of the stream reforming unit commonly associated with methanol synthesis. In other instances it may find its optimum use when combined with the initial natural gas or hydrocarbon feed to the stream reformer for the recovery of the methane, carbon monoxide and carbon dioxide values present therein.

Control of the differential pressures between the purge gas stream contacting the outside of the hollow fiber membranes and the permeated recovered synthesis gas stream withdrawn from the bores of such membranes may be achieved by any convenient method. One suitable method of such control involves adjusting the pressures maintained by the pressure control valves in the respective streams. Total flows of the respective streams can also be controlled by means of flow control valves. In order to minimize recompression and the expense thereof one very suitable method to control such differential pressures will involve establishing a minimum pressure required in the permeated recovered synthesis gas stream for its recombination at a suitable point with the fresh methanol synthesis gas stream and varying by means of a pressure controller from a pressure just sufficient to establish permeation across the membrane up to the pressure at which the purge gas stream is separated from the uncondensed reaction gas mixture. In a typical low pressure methanol synthesis such pressures may typically comprise 25 atmospheres for the permeated recovered gas stream and range from about 27 atmospheres up to about 50 atmospheres, the pressure of the purge gas stream as it is separated in such typical process. During operation of the process if total flow of synthesis gas is for some reason diminished, adjustment can be made by restricting the flow of the permeant shell effluent gas stream and, consequently, the flow of the permeated recovered gas stream, or by varying the total surface area of membranes contacted by cutting out one or more parallel membrane separator vessels without the necessity of changing the pressures imposed on each stream or the pressure differential between them. Other suitable means of control which can be employed if desired, include control to a specific content of one or other of the desired gases as determined by analysis of such gases and effected by varying pressure differentials, flow rates and/or total membrane surface areas.

The following examples are provided to further illustrate the invention. All parts and percentages of gases are by volume, unless otherwise indicated.

EXAMPLE I

In this example and in Examples II and III which follow, methanol synthesis purge gas streams of varied composition drawn from an operating low pressure methanol synthesis process were treated in a separator vessel containing hollow fiber membranes. The separator vessel contained poly(siloxane)-coated anisotropic polysulfone hollow fiber membranes prepared substantially in accordance with the method disclosed in Example 64 of Belgian Patent 660,811 issued May 16, 1978 Henis et al. The polysulfone had a molecular weight in excess of 10,000 and the poly(siloxane) a molecular weight in excess of 1000 prior to crosslinking same. The hollow fiber membranes coated on the outer surface with poly(siloxane) had an inside diameter of 250 microns, an outside diameter of 500 microns, and a wall thickness of 125 microns. The hollow fiber membranes in the separator vessel had an effective surface area of 21.6 $cm^2$. Purge gas samples were taken by direct sample tap of the recycle line of the uncondensed reaction gas mixture of an operating low pressure methanol synthesis process. Any condensate present was drained from the sample line and the gas sample allowed to flow to a gas cylinder via a high pressure coupling. After the gas pressures in the cylinder and the recycle synthesis gas line had equalized the gas cylinder was disconnected and employed to supply a sample of purge gas to the membrane separator.

Each cylinder of sample purge gas was individually analyzed by means of a gas chromatograph. Because of the pressure drop from the sample cylinder to the membrane separator. The water and methanol vapor content of the purge gas samples were well below saturation and the content of these vapors in the various purge gas samples were not determined. Pressures of the purge gas stream and of the permeant or effluent and permeate or recovered synthesis gas streams were constantly controlled. Compositions of both the permeant and permeate gas streams were determined by gas chromatographed analysis taken on continuous flow samples piped from the hollow fiber membrane module and in which at least three consecutive samples were identical in composition indicating steady state operation over an average of a 30 minute time span. Recorded analyses were determined by attaching an evacuated gas collecting bomb to the sample gas line. The gas in the filled bomb was analyzed by gas chromatograph equipped with an integrator and computerized readout of the final results.

Accuracy of component analysis is estimated at plus or minus 1% relative.

The above membrane separation unit was operated in co-current axial flow for a total period of over 950 hours of operation. It was operated at a temperature of 39°–42° C. to approximate the normal operating temperature in the synthesis gas recycle and purge gas lines of the operating plant.

The results of operating the membrane separator under varied pressure differentials, expressed as ΔP in atmospheres, are set out in Table 1 below.

Table 1

| Variations of Differential Pressure | | | | | |
|---|---|---|---|---|---|
| | | \multicolumn{4}{c}{Permeate Composition at ΔP, Atm.} | | | |
| Component, Mol % | Feed | 6.81 | 13.6 | 20.4 | 26.9 |
| $H_2$ | 63.6–63.8 | 92.6 | 92.0 | 90.5 | 89.6 |
| $CO_2$ | 6.5–6.6 | 5.3 | 5.4 | 6.2 | 6.2 |
| CO | 4.7 | 0.3 | 0.4 | 0.5 | 0.7 |
| $N_2$ | 1.8 | 0.1 | 0.2 | 0.2 | 0.2 |
| $CH_4$ | 23.2–23.4 | 1.7 | 2.0 | 2.7 | 3.5 |
| Vol. % of $H_2$ Recovered in Permeate | | 32.1 | 43.5 | 57.5 | 68.2 |

It will be observed that only modest changes in the composition of the permeate stream occur even though the differential pressures across the hollow fiber membranes were varied from 6.8 to 26.9 atmospheres (100 to 395 psi).

EXAMPLE II

The same membrane separation unit was operated in the same manner as set out in Example I at frequent intervals over an extended period utilizing cylinders of methanol synthesis process purge gas of varied composition. The reported samples of purge gas were taken respectively after 145,439 and 951 hours of operation of the same membrane separator. In all instances the pressure differential was maintained at 6.8 atmospheres (100 psig) with a pressure of 1 atmosphere on the permeate stream in the bores of the hollow fiber membrane. Temperature in each of the runs was maintained at 40°–41° C. The composition of the varied purge gas streams subjected to treatment and of the permeate streams derived from each, expressed as mole percent of each constituent gas, is set out in Table 2 below.

Table II

| Varied Methanol Purge Gas Composition | | | |
|---|---|---|---|
| Case | I | II | III |
| Purge Gas Composition, Mol % | | | |
| $H_2$ | 63.6 | 75.7 | 84.8 |
| $CO_2$ | 6.6 | 8.6 | 5.2 |
| CO | 4.7 | 6.8 | 4.5 |
| $N_2$ | 1.8 | 0.5 | 0.6 |
| $CH_4$ | 23.4 | 8.4 | 4.9 |
| Permeate Composition, Mol % | | | |
| $H_2$ | 92.6 | 93.1 | 96.5 |
| $CO_2$ | 5.3 | 6.0 | 3.2 |
| CO | 0.3 | 0.5 | 0.2 |
| $N_2$ | 0.2 | 0.1 | 0.1 |
| $CH_4$ | 1.7 | 0.4 | 0.2 |
| Vol. % of available $H_2$ in Permeate | 32.1 | 41.3 | 35.7 |
| Vol. % of Purge Gas in Permeate | 22.1 | 33.6 | 31.4 |

It will be observed that the premeate gas streams are of remarkably consistent composition when the variation in the respective purge gas compositions is considered.

EXAMPLE III

The hollow fiber membrane separator is operated as described above using samples of purge gas withdrawn from an operating methanol synthesis plant for a total period of more than 950 hours. Gas chromatographic analyses of the purge gas streams and of the shell permeant and permeated recovered synthesis streams were conducted at intervals as required by any indicated change in process conditions as well as with every change of sample gas cylinders. For each such analysis of feed and product gases the intrinsic permeabilities (P/1) for the key component gases, hydrogen, carbon dioxide and methane, were determined. The intrinsic permeability or permeability coefficient of a membrane to a specific gas is determined by the relationship P/1 where P is the permeability defined as the cubic centimeters of gas passing through the membrane per square centimeter of surface area per second for a partial pressure drop of one centimeter of mercury per unit thickness, and 1 is the thickness of the membrane in centimeters. The intrinsic permeabilities or permeability coefficients for the key component gases of the hollow fiber membranes are found to be remarkably uniform with no signs of decline in such permeabilities after over 950 hours of operation. The results of the determination of intrinsic permeabilities P/1 are set out in Table 3 below.

Table 3

| Component | P/1 of Component Gases P/1 × $10^{-5}$ after Hours: | | | | |
|---|---|---|---|---|---|
| | 25 | 145 | 439 | 703 | 951 |
| $H_2$ | 7.05 | 6.82 | 7.33 | 7.23 | 7.17 |
| $CO_2$ | 2.34 | 2.70 | 2.80 | 2.76 | 2.73 |
| $CH_4$ | 0.23 | 0.18 | 0.12 | 0.19 | 0.16 |

EXAMPLE IV

The intrinsic permeabilities, P/1, of cellulose acetate hollow fiber membranes having an external diameter of 450 microns, an internal diameter of 250 microns and a wall thickness of 100 microns were determined for the principal component gases of a methanol synthesis process purge stream of the following composition:

| | Mol. % |
|---|---|
| Hydrogen | 59 |
| Carbon Dioxide | 9 |
| Methane | 23 |
| Carbon Monoxide | 9 |

The precent recovery of the hydrogen present and the percent rejection of the methane present in the purge gas stream were determined by computer simulation for treatment of 195 kg. mols/hr of this gas stream over two different total surface areas of the above cellulose acetate hollow fiber membranes, 1395 square meters and 2325 square meters. The results of such determination are set out in Table 4 below.

Table 4

| | Cellulose Acetate Hollow Fiber Membranes | | |
|---|---|---|---|
| | | 1395m² % | 2325m² % |
| | P/1 × $10^{-5}$ | Recovery-Rejection | Recovery-Rejection |
| $H_2$ | 7.0 | 36.1 | 48.5 |
| $CH_4$ | .15 | 93.8 | 89.0 |

EXAMPLE V

A methanol synthesis process operated at steady state with a total methanol synthesis gas throughput of approximately 6800 kg.-mols per hour and a purge gas stream of approximately 370 kg.-mols per hour removed from the recycling uncondensed reaction gas line and directed to fuel. The purge gas stream was thoroughly analyzed and its composition determined at steady state operation. The compositions of a permeated recovered synthesis gas stream and a permeant fuel gas stream were determined based upon computer calculations employing a membrane separation unit composed of identical hollow fiber membranes to those described in Example 1. The hollow fiber membranes comprise anisotropic polysulfone hollow fiber membranes, the polysulfone having a molecular weight in excess of 10,000, the outer surfaces coated with poly(siloxane), which has a molecular weight in excess of 1,000 prior to crosslinking to provide a silicone rubber, produced as described in Example 1. The hollow fiber membranes have the dimensions there described. The separation units contain the number of such hollow fiber membranes to provide a total surface area of approximately 5600 square meters.

In operation of the improved process for increased methanol recovery the volume of purge gas removed from the uncondensed reaction gas recycle line is increased to 493.5 kg.-mols per hour in order to provide for the removal of the same amount of methane as in the previous operation. The pressure of the purge gas stream is the same as the recycling uncondensed reaction gases and is maintained at 46.7 atmospheres. The purge gas stream is passed first to a demister unit, a packed column suitably sized for the removal of all liquids entrained with the purge gas stream. Thereafter the purge gas stream is passed directly to the shell of the hollow fiber membrane separation unit or units in parallel comprising a cylindrical shell containing one or more bundles of the above-described hollow fiber membranes suitably manifolded for the removal of the permeate gas stream from the bores thereof and with appropriate purge gas inlet and permeant outlet ports. In the membrane separation unit or units the purge gas stream is split into two portions consisting of shell effluent gas and permeated recovered synthesis gas streams.

Utilizing the experimentally determined intrinsic permeabilities (P/1) of each of the constituent gases in the purge gas stream the compositions of the permeated synthesis gas stream at a pressure of 25.8 atmospheres and of the nonpermeated shell effluent gas stream at 46.4 atmospheres pressure are determined by computer simulation and are set out in Table 5 below. In Table 5 the compositions of these two gas streams may be compared to the composition of the purge gas stream which is set out at both the original and the increased purge gas rate.

Table 5

| | Composition of Gas Streams, kg-mol/hr. | | | |
|---|---|---|---|---|
| | Purge Gas [46.7 atm.] | | Rec. Syn. Gas | Permeant Gas to fuel |
| | Prior | New | [25.8 atm.] | [46.4 atm.] |
| $H_2$ | 234.60 | 314.77 | 215.41 | 99.39 |
| $CO_2$ | 32.53 | 43.64 | 29.23 | 14.41 |
| CO | 22.32 | 29.95 | 7.64 | 22.32 |
| $CH_4$ | 69.73 | 93.54 | 23.82 | 69.73 |
| $N_2$ | 5.06 | 6.82 | 1.73 | 5.09 |
| $H_2O$ | 0.36 | 0.49 | 0.28 | 0.21 |
| $CH_3OH$ | 3.20 | 4.25 | 2.42 | 1.83 |
| kg mol/hr | 367.80 | 493.46 | 280.52 | 212.96 |

The permeated recovered synthesis gas stream amounting to some 280 kg.-mol/hr is withdrawn from the bores of the hollow fiber membrane and manifold header and directed to the pressure stage of the fresh methanol synthesis gas operation. The pressure between the first and second stage of compression of the methanol synthesis gas at this point is approximately 25 atmospheres and the recovered synthesis gas can conveniently be combined therewith. The combined streams will thereafter be subjected to compression and circulation to the methanol synthesis catalyst in the usual manner. The permeant or shell effluent gas stream comprising about 213 kg.-mol/hr is directed to a fuel gas header for eventual use as burner fuel for the stream reforming process. It will be observed from Table 5 that the increase in volume of purge gas removed from the recycling reaction gas line is sufficient to provide for the same amount of methane rejected from the recycled recovered synthesis gas and directed to fuel as in the prior process. Therefore the purge rate of the methane and other inert gases is maintained in balance in the total circulating methanol synthesis gas system.

There can be thus recovered by means of this invention a total of 215 kg.-mol/hr of hydrogen and some 29 kg.-mol/hr of carbon dioxide as well as approximately 7.5 kg.-mol/hr of carbon monoxide, all of which gases are available for the synthesis of additional methanol. In order that the optimum amount of methanol is realized from these recovered gases there is added to the recovered synthesis gas stream some 15.85 kg.-mol/hr of carbon dioxide from an external sources which has been brought to the same pressure. This combined gas stream is forwarded to combine with the fresh methanol synthesis gas stream at the interstage compressor. At the balanced stoichiometric ratio thereby provided additional methanol in the amount of some 45 kg.-mol/hr will be realized.

In an alternative to the above process the purge gas stream after removal from the recycling uncondensed reaction gas stream is directed to a packed column water scrubber which absorbs from the purge gas stream 95% of the methanol present as vapor in the purge gas stream. The water and methanol solution from the scrubber is directed to the distillation column of an associated crude methanol purification unit where such absorbed methanol is recovered. The scrubbed purge gas is then directed to a demister unit which removes any entrained water from the purge gas and thence to the membrane separation unit as described above. The resulting recovery of added methanol, amounting to some 49 kg.-mol/hr from increased methanol synthesis from the recovered hydrogen and carbon dioxide synthesis gas and methanol recovered in the water scrubber is set out in Table 6 below.

Table 6

| Methanol Synthesis | Comparison of Methanol Recovery, kg-mol/hr | | | |
|---|---|---|---|---|
| | Rec. Syn. Gas | Added | Purge Gas | Methanol |
| $H_2$ | 215.41 | | | |
| $CO_2$ | 29.23 | 15.85 | | 45.05 |
| Methanol Recovery | | | 4.25 | |
| via Scrubber | | | | 4.04 |
| Total Added Methanol | | | | 49.09 |

What is claimed is:

1. In a methanol synthesis process wherein methanol is synthesized from a synthesis gas comprising hydrogen and carbon dioxide by passing said synthesis gas over a methanol synthesis catalyst at methanol-forming conditions to form a gaseous mixture including methanol, water and unreacted carbon dioxide, said gaseous mixture is cooled, methanol and water are condensed therefrom and separated from the uncondensed gaseous mixture, a portion of said uncondensed gaseous mixture is removed as purge gas and the remaining uncondensed gaseous mixture is recycled to contact said methanol synthesis catalyst, the improvement comprising contacting said purge gas with the outside surfaces of a plurality of hollow fiber membranes selectively permeable to both hydrogen and carbon dioxide to form a permeant gas stream depleted in hydrogen and carbon dioxide and a permeate gas stream enriched in both said gases, and combining said enriched permeate gas stream with said synthesis gas.

2. The process of claim 1 wherein said removed purge gas is treated to recover methanol vapor therein prior to contacting said purge gas with said membranes.

3. The process of claim 2 wherein said methanol vapor is absorbed in a water scrub.

4. The process of claim 3 wherein said absorbed methanol is recovered by distillation.

5. The process of claim 1 wherein carbon dioxide gas is added to said enriched permeate gas stream.

6. The process of claim 5 wherein said carbon dioxide gas is added in an amount substantially equivalent to the stoichiometric excess of hydrogen over carbon oxides in said enriched permeate gas stream.

7. The process of claim 1 wherein a pressure differential of from about 3 to about 100 atmospheres is maintained between said purge gas and said permeate gas stream.

8. The process of claim 7 wherein said permeate gas stream is maintained at a pressure of at least about 25 atmospheres and combined with said synthesis gas at substantially the same pressure.

9. The process of claim 1 wherein said hollow fiber membranes have outside diameters of from about 150 to about 800 microns and a wall thickness of about 50 to about 300 microns.

10. The process of claim 1 wherein said membranes are multicomponent hollow fiber membranes which comprise a porous hollow fiber separation membrane and a coating in occluding contact with the outside surface thereof.

11. The process of claim 10 wherein said separation membrane comprises polysulfone and said coating comprises poly(siloxane).

12. In a methanol synthesis process wherein methanol is synthesized from a synthesis gas comprising hydrogen and carbon dioxide by passing said synthesis gas over a methanol synthesis catalyst at methanol-forming conditions to form a gaseous mixture including methanol, water and unreacted carbon dioxide, said gaseous mixture is cooled, methanol and water are condensed therefrom and separated from the uncondensed gaseous mixture, a portion of said uncondensed gaseous mixture is removed as purge gas and the remaining uncondensed gaseous mixture is recycled to contact said methanol synthesis catalyst, the improvement comprising contacting said purge gas with the outside surfaces of a plurality of hollow fiber membranes selectively permeable to both hydrogen and carbon dioxide and having an outside diameter of from about 150 to 800 microns and a wall thickness of from about 50 to 300 microns to form a permeant gas stream depleted in hydrogen and carbon dioxide and a permeate gas stream enriched in both said gases, and combining said enriched permeate gas stream with said synthesis gas.

13. The process of claim 12 wherein said removed purge gas is treated to recover methanol vapor therein prior to contacting said purge gas with said membranes.

14. The process of claim 13 wherein said methanol vapor is absorbed in a water scrub and recovered by distillation.

15. The process of claim 12 wherein carbon dioxide gas is added to the enriched permeate gas stream.

16. The process of claim 15 wherein said carbon dioxide gas is added in an amount substantially equivalent to the stoichiometric excess of hydrogen over carbon oxides in said permeate gas stream.

17. The process of claim 12 wherein a differential in pressure of from about 3 to about 100 atmospheres is maintained between said purge gas and said permeate gas stream.

18. The process of claim 12 wherein said purge gas is maintained at a pressure of from about 30 to about 100 atmospheres.

19. The process of claim 12 wherein said permeate gas stream is maintained at a pressure of from about 10 to about 30 atmospheres.

20. The process of claim 12 wherein said membranes are multicomponent hollow fiber membranes which comprise a porous hollow fiber separation membrane and a coating in occluding contact with the outside surface thereof.

21. The process of claim 20 wherein said porous separation membrane comprises polysulfone and said coating comprises poly(siloxane).

22. The process of claim 20 wherein said porous separation membrane comprises polysulfone having a molecular weight of at least about 10,000 and said coating comprises poly(siloxane) cross-linked to provide a silicone rubber.

23. In a methanol synthesis process wherein methanol is synthesized from a synthesis gas comprising hydrogen and carbon dioxide by passing said synthesis gas over a methanol synthesis catalyst at methanol-forming conditions to form a gaseous mixture including methanol, water and unreacted carbon dioxide, said gaseous mixture is cooled, methanol and water are condensed therefrom and separated from the uncondensed gaseous mixture, a portion of said uncondensed gaseous mixture is removed as purge gas and the remaining uncondensed gaseous mixture is recycled to contact said methanol synthesis catalyst, the improvement comprising contacting said purge gas with the outside surfaces of a plurality of hollow fiber membranes selectively permeable to both hydrogen and carbon dioxide and having an outside diameter of from about 150 to 800 microns and a wall thickness of from about 50 to 300 microns to form a permeant gas stream depleted in hydrogen and carbon dioxide and a permeate gas stream enriched in both said gases, adding carbon dioxide gas to the enriched permeate gas stream, and combining said enriched permeate gas stream with said synthesis gas.

24. The process of claim 23 wherein said carbon dioxide gas is added to the enriched permeate gas stream in an amount substantially equivalent to the stoichiometric excess of hydrogen over carbon oxides in said permeate gas stream.

25. The process of claim 23 wherein said membranes are multicomponent hollow fiber membranes which comprise a porous hollow fiber separation membrane and a coating in occluding contact with the outside surface thereof.

26. The process of claim 25 wherein said porous separation membrane comprises polysulfone and said coating comprises poly(siloxane) cross-linked to provide a silicone rubber.

27. The process of claim 1 wherein said enriched permeate gas stream is combined with said synthesis gas before final compression of said synthesis gas to methanol synthesis pressure.

28. The process of claim 12 wherein said enriched permeate gas stream is combined with said synthesis gas before final compression of said synthesis gas to methanol synthesis pressure.

29. The process of claim 23 wherein said enriched permeate gas stream is combined with said synthesis gas before final compression of said synthesis gas to methanol synthesis pressure.

30. The process of claim 23 wherein methanol vapor in said purge gas is absorbed in a water scrub prior to contacting said purge gas with said membranes.

* * * * *